United States Patent [19]

Kelly

[11] Patent Number: 5,290,684
[45] Date of Patent: Mar. 1, 1994

[54] PERMANENT HUMAN HEPATOCYTE CELL LINE AND ITS USE IN A LIVER ASSIST DEVICE (LAD)

[75] Inventor: James H. Kelly, Houston, Tex.

[73] Assignee: Baylor College of Medicine, Houston, Tex.

[21] Appl. No.: 965,448

[22] Filed: Oct. 23, 1992

Related U.S. Application Data

[63] Continuation-in-part of Ser. No. 524,075, May 16, 1990.

[51] Int. Cl.$^5$ .......................... C12Q 1/02; C12N 5/00
[52] U.S. Cl. ................................. 435/29; 435/240.2; 435/240.23; 435/240.242
[58] Field of Search .................. 435/29, 240.2, 240.23, 435/240.242

[56] References Cited

U.S. PATENT DOCUMENTS

| | | | |
|---|---|---|---|
| 3,935,066 | 1/1976 | Apostolov | 435/240.23 |
| 4,393,133 | 7/1983 | Knowles | 435/6 |
| 4,416,986 | 11/1983 | Markus | 435/240.242 |
| 4,853,324 | 8/1989 | Viles | 435/2 |

OTHER PUBLICATIONS

Bertolotti, R., A Selective System for Hepatoma Cells . . . Somatic Cell Genetics, 3 #4, 1977, pp. 365-380.
Knowles, Human Heptacellular Carcinoma Cell Lines . . . Science, vol. 209, 25 Jul. 1980, pp. 497-499.
Miura Y., In Vitro Maintenance of Terminal . . . Artificial Organs 11(5): 361-365, 1987.
Saito S., A New Hybrid Artificial Liver Using . . . Trans Am Soc Artif Intern Organs 33: 459-462 (1987).
Gerlach, Use of Hepatocytes in Adhesion & Suspension . . . Inter J. Artif Organs 12; 788-792 (1989).
Zhai, W., A Nude Mouse Model for the In Vivo Production . . . Gastro 98 (1990) pp. 470-477.
Yanagi K., Performance of a New Hybrid Artificial . . . . Trans Am Soc Artific Internal Organs 35: 570-572 (1989).
Chui, J., The Formations of Bile Canaliculi in Human . . . . Hepatology 11 (5) 1990, pp. 834-842.
Sussman et al, *Hepatology, 16(1): 60-65 (1992)*.
Kelly et al, *Artif. Organs, 16(4): 418-422 (1992)*.
Kelly et al, *Hepatology, 15(2): 329-336 (1992)*.

*Primary Examiner*—Michael G. Wityshyn
*Assistant Examiner*—Ralph Gitomer
*Attorney, Agent, or Firm*—Sughrue, Mion, Zinn, Macpeak & Seas

[57] ABSTRACT

Permanent cell lines are provided which display liver-specific biological activity at a level effective to support a subject suffering from hepatic failure or insufficiency. The cells find use in treating various liver disorders. An example of the cell lines is HepG2/C3A deposited under ATCC No. CRL-10741. Methods for use of the cells in liver assist devices and methods for producing liver assist devices are also provided.

24 Claims, 9 Drawing Sheets

METHIONINE UPTAKE BY HEP G2 CELLS

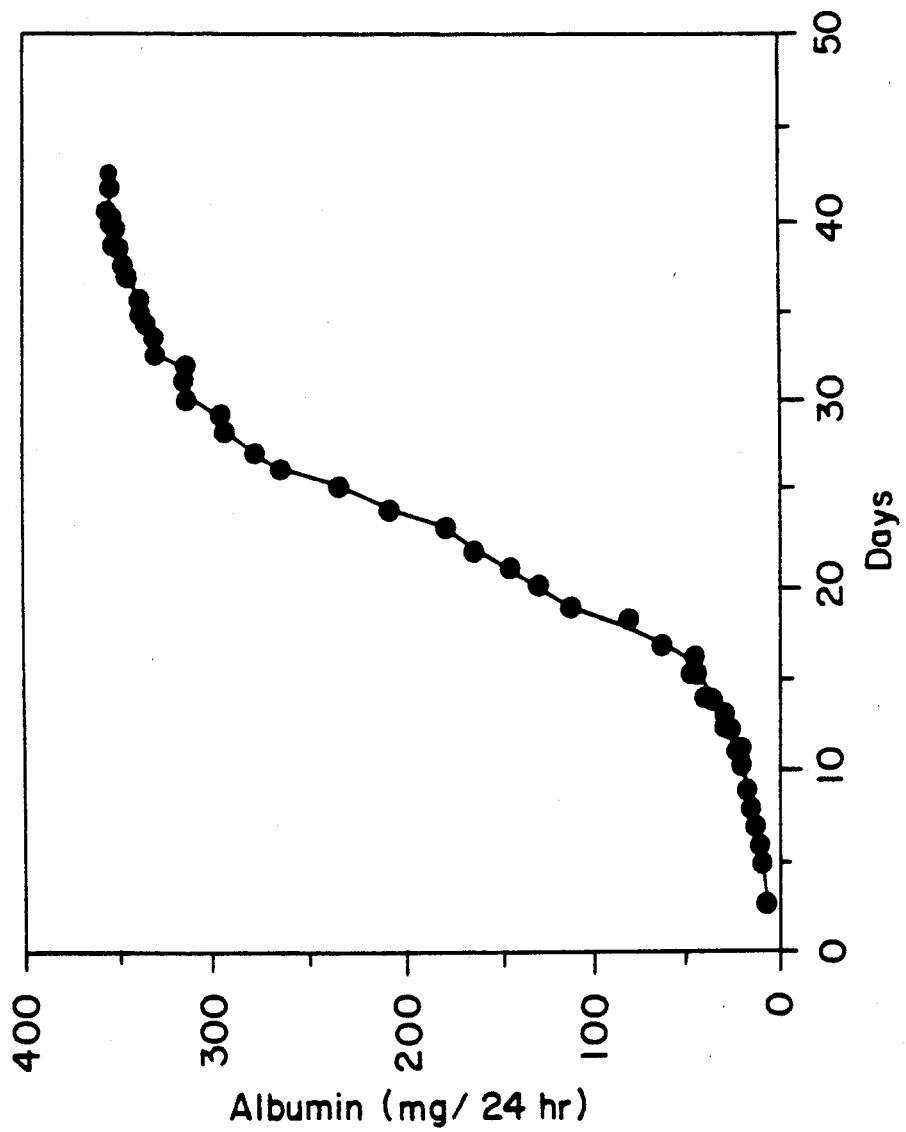

PERMANENT HUMAN HEPATOCYTE CELL LINE AND ITS USE IN A LIVER ASSIST DEVICE (LAD)

This invention was made with Government support; the Government has certain rights in the invention.

This is a continuation-in-part of U.S. patent application Ser. No. 07/524,075, filed May 16, 1990.

FIELD OF THE INVENTION

The invention in the field of cell biology and medicine relates to a permanent cell line of hepatocytes with normal liver functions and methods of their use, particularly the use of the cell line in liver assist devices and in studying metabolism and regulation of liver cells.

BACKGROUND OF THE INVENTION

Fulminant hepatic failure (FHF), defined as severe hepatocellular dysfunction in which encephalopathy occurs within eight weeks of the onset of symptoms (Bernau, J. et al. *Sem. Liv. Dis.* 6:97-106 (1986); Yanda, R. J. *West. J. Med.* 149:586-591 (1988); Katelaris, P. H. et al. *Med. Clinics N. Amer.* 73:955-970 (1989)), is generally caused by viral hepatitis, drug reactions or poisoning. In the absence of liver transplantation, the survival rate is about 20% but varies dramatically (from 6 to 79%) depending on age of the patient and etiology of the disease (Bernau et al., supra; Yanda, supra; Katelaris et al., supra).

The clinical course of FHF is influenced by the onset of multi-organ failure and mortality increases with the onset of severe clotting abnormalities, renal failure, pulmonary edema or cardiovascular collapse (Bihari, D. J. et al. *Sem. Liv. Dis.* 6:119-128 (1986)). The development of multi-organ failure is the result of circulating toxins such as mercaptans, phenols, fatty acids, ammonia and molecules which increase vascular permeability (Bernau et al., supra; Yanda, supra; Katelaris et al., supra). The most severe consequence of this increased permeability is seen in the brain. Toxins cross the blood-brain barrier and produce effects like the inhibition of $Na^+-K^+$ ATPase and a depression of the level of consciousness by occupation of the GABA-benzodiazepine receptor (Bassett, D. J. et al. *Gastroenterology* 93:1069-1077 (1987)). The final step in this progressive central nervous system disturbance is cerebral edema, the most common cause of death in FHF (Ede, R. J. et al. *Sem. Liv. Dis.* 6:107-118 (1986)).

Orthotopic liver transplantation is an effective treatment for a wide variety of conditions that destroy hepatic function ranging from genetic defects to tumors (Starzl, T. E. et al. *N. Engl. J. Med.* 321:1014-1022 (1989)). This is an increasingly popular treatment in the United States, with approximately 2000 transplants per year and an expected rise to 4000 per year within the next few years in the U.S. and a similar number in Europe. It has been estimated that, were the financial and medical resources available, the actual need could reach as high as 50,000 liver transplants per year in the U.S. alone.

One of the major problems with transplantation is the fairly fine distinction between a sufficient and insufficient amount of liver function. For example, a rat typically survives a 70% hepatectomy whereas removal of 80% of the liver is generally lethal. The consequence of this fact is that patients frequently enter into FHF precipitously. Since no satisfactory method for artificial liver support is currently available, therapeutic decisions are often made on the basis of locally available medical resources and without the ability to obtain consent of the patient.

The reversal of multi-organ failure by orthotopic liver transplantation has made it the standard of therapy against which other therapeutic modalities will have to be measured. Liver transplantation has been advocated in all patients who present in FHF based on the observation that, when transplantation was delayed until its need became obvious, 60% of patients died.

This possibly overzealous view ignores the fact that FHF is not uniformly fatal. Groups with a relatively good prognosis, such as acetaminophen poisoning patients, have been identified. Since recovery from FHF is usually associated with the return of normal liver function, and transplantation commits the patient to lifelong medical supervision and immunosuppression, early transplantation cannot be considered the best option unless a fatal outcome can be predicted early in the course of illness.

On the other hand, emergency transplantation is also unsatisfactory. Patients entering stage III coma are at an immediate increased risk of death, with their condition often deteriorating rapidly. This may necessitate transplanting a liver from an incompatible donor. Indeed, several deaths due to failed organ procurement have been reported (Vickers, C. et al. *J. Hepatol.* 7:143-150 (1988); Esmond, J. C. et al. *Gastroenterology* 96:1583-1588 (1989)).

Emergency orthotopic liver transplantation is currently the only method of acute liver support known in the art. It has a high mortality rate, a prohibitive cost, and a significant negative impact on the patient's quality of life. An alternative method of supporting liver function would be highly desirable in that it could provide sufficient time for liver regeneration to occur. The benefit to the individual is beyond any reasonable calculation, but the financial savings amount to hundreds of thousands of dollars; the actual cost of the transplant alone is between $70,000 and $240,000 depending on the condition of the patient (Dindzans, V. J. et al. *Dig. Dis. and Sci.* 34:161-166 (1989)).

Since secondary liver damage may be caused by circulating toxins, early hepatic support may also improve the internal milieu thereby promoting liver regeneration. In cases where regeneration does not occur, liver support will forestall or prevent multi-organ failure. Thus, the fear of "watching" the patient too long and the death of patients awaiting a donor would be minimized by the availability of a liver assist device. Furthermore, only patients whose livers fail to regenerate will be transplanted, and improvement of general health prior to liver transplantation surgery is correlated with improved survival.

In 10 to 20% of liver transplants, the transplanted liver fails on reperfusion. These patients then require emergency second transplants. The availability of an extracorporeal liver assist device would allow them to recover before undergoing a second round of major surgery. A means of supporting liver function is therefore urgently required.

The use of artificial support devices has had dramatic effect on kidney, heart and lung transplantation, but no such device is available for liver support. There remains, therefore, the need for a supportive system for long-term preservation of liver functions. Such a liver assist device would have application in a number of transplant situations. First, it would allow patients in fulminant hepatic failure to be stabilized and calmly evaluated before operating. Second, it finds use in stabilizing and assisting patients after transplant, particularly in situations in which the graph fails to respond on reperfusion. Third, in some instances it may serve as a substitute for transplant. The device would allow time for the patient's natural liver to regenerate, sparing the expense of operation, the life long dependence on immunosuppression and the likelihood of premature mortality.

Related Literature

The human hepatoma cell line HepG2 is disclosed in U.S. Pat. No. 4,393,133. Further experiments utilizing the HepG2 cell line are reported by Kelly et al., *In Vitro Cell. and Dev. Biol.* 25:217-222 (1989), and Darlington et al., *In Vitro Cell. and Dev. Biol.* 2-3:349-354 (1987). The human hepatoma cell line, HuH-7, is discussed in Nakabayashi et al., *Cancer Research* 42:3858-3863 (1982).

A review article on artificial livers is discussed by Jauregui et al., in *Biocompatible Polymers, Metals, and Composites*, M. Szycher, Ed., Technical Pub, Lancaster, Pa., pp. 907-928 (1983).

Liver assist devices disclosed in the prior art include U.S. Pat. No. 4,853,324; U.S. Pat. No. 4,675,002; U.K. Patent Application No. GB2,211,857,A; European Patent Application Publication No. 0 079 781; Ehrlich et al., *In Vitro* 14:443-450 (1978); Wolf et al., *Trans. Amer. Soc. Artif. Int. Organs*, Volume XXI:16-27 (1975); Wolf et al., *International Journal of Artificial Organs* 1:45-51 (1978); and, Wolf et al., *International Journal of Artificial Organs* 2:97-103 (1979).

Encapsulation of tissue cells or hepatocytes can be found in U.S. Pat. No. 4,391,909; U.S. Pat. No. 4,353,888; Sun et al., *Trans Am. Soc. Artif. Intern. Organs*, Volume XXXI:39-41 (1986); and, Cai et al., *Artificial Organs* 12:388-393 (1988).

A cell culture device for use as an artificial pancreas is disclosed in U.S. Pat. No. 4,242,460.

SUMMARY OF THE INVENTION

The present invention is drawn to permanent cell lines which constitutively provide liver specific biological activity at a level effective to support a subject suffering from hepatic failure. The cells are clonally derived from a hepatoblastoma cell line and exhibit many of the characteristics of normal human hepatocytes. The cells are useful for treating various liver disorders. In particular, the cells are useful in liver assist devices (LAD) for treating subjects with fulminant hepatic failure. More typically, the device and methods of the invention are useful as palliative measures in patients awaiting a liver transplant.

BRIEF DESCRIPTION OF THE DRAWINGS

In FIG. 6A, the results are presented as cpm (in glycogen)/minute/g wet weight of cells. Each time point is the mean of triplicate determinations from a single experiment. Each point is based on one 850cm$^2$ roller bottle which contained approximately 2g of cells. FIG. 6B shows the ratio of $^3$H to $^{14}$C in glycogen.

FIG. 8. Albumin production by HepG2/C3A cells in the FloPath 1400 Cartridge. The cartridge was inoculated with approximately 0.5 g of cells. Twenty ml of medium was removed from the extracapillary space daily after day 5 and was assayed for human serum albumin using a solid phase radioimmunoassay (see Example VII, below). Results are expressed as total albumin produced per 24 hr.

DESCRIPTION OF THE PREFERRED EMBODIMENTS

Figure 1:
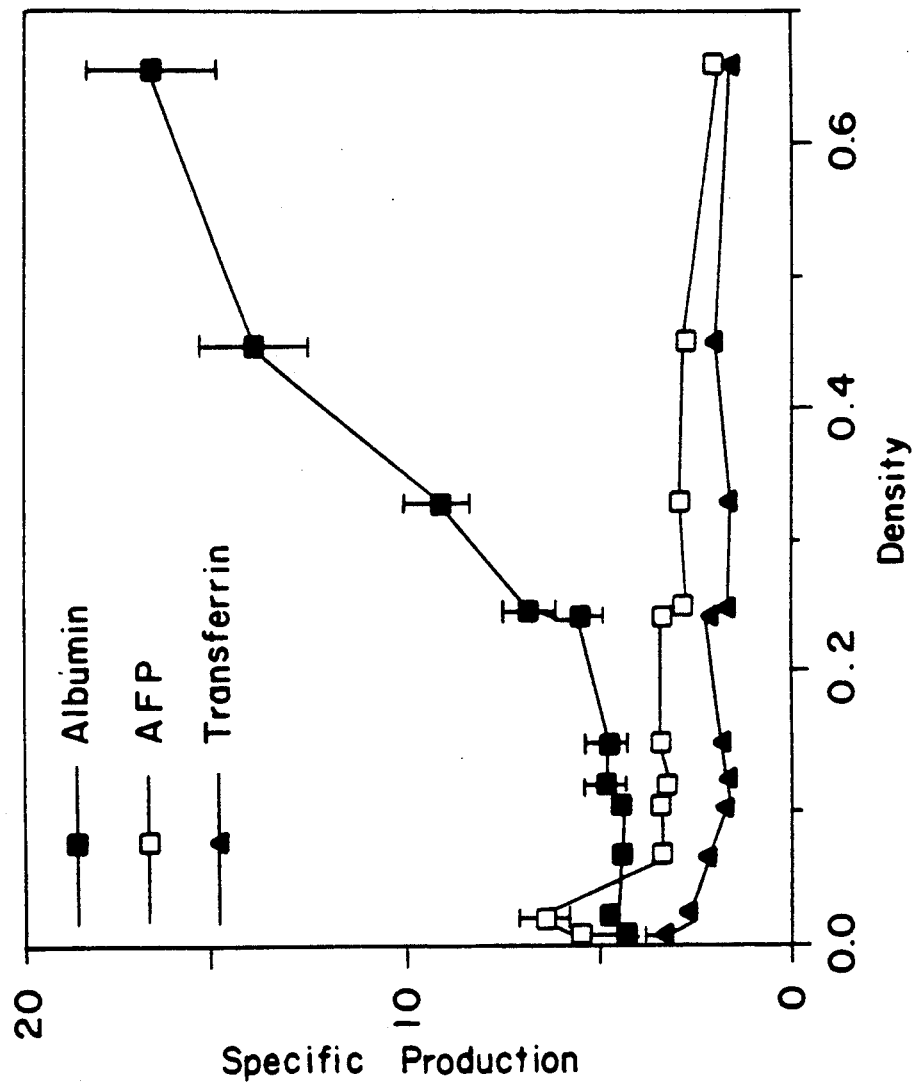
FIG. 1. Serum protein synthesis in HepG2. HepG2 cells were plated at approximately 10,000 cells/cm$^2$ and allowed to grow with daily medium change to the indicated density. The medium was removed from duplicate cultures and assayed for albumin, AFP and transferrin. Specific production is expressed as: $\mu$g protein/mg total cell protein/24 hrs. Density is expressed as mg total cell protein/cm$^2$. All values are the mean of duplicate determinations on duplicate samples. The standard deviation was less than 10% in all cases.

Novel cell lines, their preparation, and methods for their use are provided. The cell lines are liver cell lines derived from a hepatoblastoma that retain most of the characteristics of the human hepatocyte. The cell lines are able to mimic the liver both qualitatively and quantitatively. They express near normal levels of several central metabolic pathways, including glycolysis, gluconeogenesis, glycogenesis and ureogenesis. In addition, these cells synthesize near normal levels of albumin and other serum proteins, contain high levels of liver specific transcription factors, and exhibit the structures and polarity characteristic of the human hepatocyte.

The cell lines of the present invention are derived from a known hepatoblastoma cell line, HepG2. By "derived," is intended that the cell line is obtained or cloned from HepG2 by a defined selection method, provided below. The HepG2 line is a human hepatoblastoma cell line which exhibits certain characteristics of normal human hepatocytes. The cell line is disclosed in U.S. Pat. No. 4,393,133 and is available from the American Type Culture Collection (ATCC), Rockville, Md., as ATCC No. HB8065. Characteristics of the cell line have been discussed in publications including Darlington et al., *In Vitro Cellular Developmental Biology* 23:349-354; Kelly et al. *In Vitro Cellular and Developmental Biology* 25:217-222; Darlington, G. J., *Meth. Enzymol*, 151:19-38 (1987); Thrift, R. N., et al., *J. Lip. Res.* 27:236-250 (1986). Unlike most other human liver lines, HepG2 does not carry any human hepatitis B virus (HBV) genetic sequences. Thus, the cell lines of the invention, clonally derived from HepG2, do not carry any HBV genetic sequences. Further, the cell lines are tumorigenic. They are derived from HepG2 which forms tumors in nude mice.

The cell lines of the present invention may be obtained from the HepG2 line by selecting for cells which show: (1) a strong contact inhibition; (2) high expression of albumin; (generally at least about 20 μg/mg total cell protein/24 hr, more generally at least about 25 μg/mg total cell protein/24 hr); and (3) high albumin to alphafetoprotein ratio at confluence (generally a ratio of at least about 15, more generally at least about 25). Details on the methods for selection can be found in the Experimental Section. A preferred cell line, HepG2/-C3A, which has been deposited at the American Type Culture Collection under ATCC N. CRL-10741, is described more fully below.

The selected cell lines synthesize levels of human albumin and other serum proteins that are similar to levels produced by normal human hepatocytes and demonstrate regulation of gene expression as is predicted for developing or regenerating normal hepatocytes. As indicated, such cell lines are cloned by selection for high albumin production and a high albumin to alphafetoprotein (AFP) ratio when the cells reach confluence. The term confluence refers to the cells density in culture when the cells begin to contact one another and cover most or all of the available growth surface.

In the preconfluent phase of growth, selected cells behave like regenerating liver. They have a rapid doubling time (about 24 hr) and express a number of fetal proteins, including AFP, aldolase A/C and pyruvate kinase K. Upon reaching confluence, the cells assume an adult phenotype wherein cell division slows dramatically (doubling time >200 hr) and expression of fetal proteins is extinguished. Cells expressing an adult phenotype become predominant, as evidenced by production of albumin, aldolase B, and pyruvate kinase L, and development of histologic features of normal liver.

The cell lines of the present invention have several distinct advantages over hepatoma cell lines known in the prior art for the purposes of the present invention. They are extremely well differentiated. Consequently, they constitutively express liver-specific biological activities at a level effective to support a subject in hepatic failure or insufficiency for either short or long periods.

The term "constitutively" refers to the fact that these cells normally express liver-specific biological activities without any need for particular forms of induction. Once these cells reach confluence, when they grow to fill the available surface, they maintain normal liver-specific biological activities.

The term "liver-specific biological activity" as used herein refers to a number of physiological/biochemical reactions which take place specifically in hepatocytes, as well as in the cells of the present invention. Also intended by this term are the protein and lower molecular weight products which these cells synthesize and secrete.

Hepatocytes perform multiple finely-tuned functions which are critical to homeostasis. Of the variety of cell types in the mammalian body, only hepatocytes combine pathways for synthesis and breakdown of carbohydrates, lipids, amino acids, proteins, nucleic acids and co-enzymes simultaneously to accomplish a unique biological task. The key "liver-specific" biological functions include: (1) gluconeogenesis; (2) glycogen synthesis, storage and breakdown; (3) synthesis of serum proteins including albumin, hemopexin, ceruloplasmin, the blood clotting factors (including Factors V, VII, X, prothrombin and fibrinogen), cyl-antitrypsin, antithrombin III, and AFP; (4) conjugation of bile acids; (5) conversion of heme to bile pigments; (6) lipoprotein synthesis; (7) vitamin storage and metabolism; (8) cholesterol synthesis; (9) ammonia metabolism, including urea synthesis and glutamine synthesis; (10) amino acid metabolism, including metabolic conversion and re-utilization of aromatic amino acids; and (11) detoxification and drug metabolism.

The cells of the present invention are perhaps capable of performing all classes of the "liver-specific" biological functions. All functions have been tested except for classes 4 and 5. Exemplary functions include the ability to perform ammonia metabolism, amino acid metabolism, detoxification, and protein production, especially of coagulation factors. These functions are of particular importance where the cells are to be used in a liver assist device.

For support of subjects in the form of relatively short term LADS, such as FHF patients awaiting liver transplant or following liver rejection and awaiting retransplant, the four groups of liver-specific biological functions noted above are of central importance. The other functional deficits can be provided by other means (such as by provision of glucose and monitoring of glucose levels) or do not need acute attention (for example, conjugation of bile acids or bile pigment production, or drug metabolic activity).

The levels of liver-specific biological activity "effective to support" a subject suffering from hepatic failure or insufficiency are those which will result in normal or near normal levels of serum proteins, coagulation factors, amino acids, and other metabolites produced in or metabolized by the liver. These various molecules and metabolic products and the physiological as well as pathological ranges of their concentrations or levels are well known in the art and are set forth, for example, in Braunwald, E. et al., eds., *Harrison's Principles of Internal Medicine*, 11th Ed., McGraw-Hill, publisher, New York, N.Y. (1987), which is hereby incorporated by reference.

Once a particular cell line has been selected based upon the initial criteria of strong contact inhibition, high expression of albumin, and a high albumin/alphafetoprotein ratio at confluence, the cell line may then be tested for the performance of liver-specific biological functions. Thus, experiments can be performed to examine the metabolic functions of the cells, particularly in an environment in which the cells can be used as a liver assist device. Metabolic functions tested include oxygen dependence, glucose and urea synthesis, bilirubin uptake and conjugation, and clotting factor biosynthesis.

The liver is an extremely aerobic organ and accounts for 20% of the body's oxygen consumption. Like the liver in vivo, it is noted that the cultures of the present invention require oxygen for high-level liver-specific function (see Experimental section). Provision of adequate oxygenation may stimulate both growth and differentiated function in selected cells. The effect of oxygen on selected cell lines may be tested in several ways, including the following:

(1) The growth rate of the cells in continuously perfused cell culture may be examined in increasing concentrations of dissolved oxygen (4-20%). Growth rate can be examined in a standard medium containing high concentrations of glucose and in glucose-free medium containing lactate and amino acids as the only carbon source. As gluconeogenesis is exceedingly oxygen-sensitive, one would expect cell growth to be more dramatically affected in the glucose-free medium as compared to cells in the presence of glucose.

(2) Indicators of metabolic activity may also be measured in the cells at different concentrations of oxygen. Such metabolic activities include total oxygen consumption, energy charge, redox state, and the ratio of glucose consumption to oxygen consumption.

Glucose and urea synthesis are the primary means of removing excess amino acids and ammonia from the blood. Amino acid catabolism results in the liberation of carbons which are shunted into the citric acid cycle and thence to glucose. The nitrogen released during this process is used in the synthesis of urea. Therefore, a selected cell line must synthesize both glucose and urea. Methods for measurement of glucose and urea are known in the art, for example see Kershcer et al., in *Methods of Enzymatic Analysis*, H. U. Bergmyer, ed., 3rd ed., Verlag Chemie, Weinheim, Vol. VII, pp. 59-67 (1983).

Elevated serum bilirubin is a highly visible indicator of liver disease. While not generally toxic in adults, high circulating levels of unconjugated bilirubin may produce brain damage and even death in neonates. This condition is known as kernicterus because of the typical yellow appearance of the brain stem nuclei at postmortem examinations. The ability of the selected cell lines to metabolize bilirubin may be examined, for example, using oxygenated monolayer cultures. For this test, serum from patients with hyperbilirubinemia will be incubated with oxygenated cells to determine whether the cells are able to conjugate the bilirubin. Direct binding studies may be carried out using [$^3$H]-bilirubin in the presence and absence of unlabeled competitor in order to determine $V_{max}$ and $K_m$.

The cell lines are also tested for clotting factor biosynthesis. Many of the clotting factors are synthesized by the liver, and the development of a severe coagulopathy is an ominous sign in FHF. Although all of the vitamin K dependent group is affected, antithrombin III (AT III) has been identified as the most significant deficiency. The cell lines are tested for the ability to synthesize fibrinogen, prothrombin, factors VII, and X, and AT III. The levels of production of these factors may be quantitated using commercially available antibodies.

The properties of the cell lines make them particularly useful in liver assist devices (LAD). For the most part, the cells may be used in any device which provides a means for culturing the cells, as well as a means for separating the cells from blood which will be passed through the device. Membranes or capillaries are available in the literature for use which allow for the crossover of toxic solutes from the blood to the cells as well as the diffusion of vital metabolites provided by the cells across the membrane into the blood. The permiselective or semipermeable membrane additionally provides a mechanical barrier against the immune system. For the most part, a membrane or capillary will be used which features a molecular weight cutoff from about 20,000 daltons up to about 80,000 daltons, generally about 30,000 daltons to about 50,000 daltons. However, it may be preferable to utilize a membrane with pore sizes from about $0.1\mu$ to about $0.3\mu$, usually about $0.2\mu$. A pore size in this range will exclude cellular elements yet still allow proteins and protein complexes to pass through. Thus, the serum protein deficiencies of FHF, can be ameliorated.

Generally, the cells are grown in the liver assist device. After growth of the cells, the subject's blood is passed through the device, and dissolved molecular species (e.g., bilirubin) diffuse through the membrane and are taken up and metabolized by the cells. For the most part, the devices are based primarily on extracorporeal blood processing. Generally, the devices are designed to house the cells in a blood-perfused device attached to the blood stream. Typically, the device is attached to the blood stream between an artery and a vein.

Several designs of liver assist devices are known in the literature. For example, devices have been described by Viles et al., U.S. Pat. Nos. 4,675,002 and 4,853,324; Jauregin, GB 2,221,857A; Wolf et al., *International J. of Artificial Organs* 2:97-103 (1979); Wolf et al., *International J. of Artificial Organs* 1:45-51 (1978); and Ehrlich et al., *In Vitro* 14:443-450 (1978), which disclosures are herein incorporated by reference. Preferred devices include the hollow fiber cartridge and similar perfusion devices.

Bioreactors, such as hollow fiber bioreactors, may be utilized as liver assist devices. Such bioreactors, such as the Anchornet series, are known in the literature and are available commercially. See, for example, Heifetz et al., *BioTechniques* 7:192-199 (1989); and Donofrio, D. M., *Amer. Biotech. Lab.* Sept. 1989, Publication #940, which disclosures are herein incorporated by reference.

The cells of the present invention, when grown in a hollow fiber cartridge or similar perfusion device with capacities for high numbers of cells, can function as a perfused liver, allowing accurate assessment of human liver metabolism and replacement of liver-specific biological activities. Therefore, a perfusion device containing a culture of the disclosed cells is capable of functioning as a liver assist device. In one embodiment of this invention the LAD is extracorporeal, referring to its connection to arterial and venous circulation outside the body. An extracorporeal LAD (or ELAD) is particularly useful for providing temporary liver support for subjects suffering from FHF. In an alternate embodiment, the LAD is implanted in the body, that is, is "intracorporeal." This embodiment is useful, and may be advantageous, as a longer term LAD.

For use in a liver assist device, the cells are generally grown on the membrane or porous support. For the most part, the cells attach to the support upon growth. However, it is recognized that linkage materials may be provided to attach the cells to a support. Suitable linkage materials are known in the art. See, for example, GB 2,221,857A.

Hollow fiber cartridges are two-chamber units which reproduce the three-dimensional characteristics of normal organs (Knazek, R. H., *Feder. Proc.* 33:1978-1981 (1974); Ku, K. et al., *Biotechnol. Bioeng.* 23:79-95 (1983)), which references are hereby incorporated by reference. Culture or growth medium is circulated through the capillary space and cells are grown in the extracapillary space (Tharakan, J. P. et al., *Biotechnol. Bioeng.* 28:1605-1611 (1986). Such hollow fiber culture systems have been disclosed as useful for culture of hybridoma cells lines for the production of monoclonal antibodies (Altshulter, G. L. et al., *Biotechnol. Bioeng.* 28:646-658 (1986); Heifetz, H. H. et al., (*BioTechnigues* 7:192-199 (1989); Donofrio, D. M., *Amer. Bioteach. Lab.*, Sept. 1989, Publication #940)). Further, a number of other cell types, including the liver cell lines PLC/PRF 5 and Reuber hepatoma, (McAleer, W. J. et al. *J. Virol. Meth.* 7:263-271 (1983); Wolf, C. F. W. (1982)) and pancreatic islet cells (Araki, Y. et al., *Diabetes* 34:850-854 (1985)) have been cultured in this manner.

Once a device has been chosen for use as a liver assist device, it is provided with the appropriate medium and an inoculation of cells. Generally, cells are grown in a complex media, for example, in a 3/1 mixture of Eagle's MEM with Earle's salts (Gibco) and Waymouth's MAB 87/3 (Gibco) containing 10% defined/supplemented calf serum (Hyclone). The devices are then maintained in a 37° C. room with constant recirculation of medium and constant inflow of fresh medium. For use with a hollow fiber cartridge, 1400 cm$^2$, the cartridge is provided with 150 ml/min of recirculated medium with a constant inflow of about 0.5 ml/min. A 1400 cm$^2$ cartridge is generally inoculated with about $1 \times 10^9$ cells.

The function of the cells in the device can now be tested for the capability of the device to function as a liver assist device. This includes measurements of essential liver biological functions as discussed above.

For the most part, it will not be necessary to add additional oxygen to the system. However, the oxygen tension in the cultures can be determined and additional oxygen added if necessary.

In order to vary the oxygen tension in cultures of the selected cell lines to determine the optimum oxygen level, cells can be grown in a continuous perfusion apparatus. The apparatus will consist of a recirculation pump, medium bottles, and a lid that fits on a standard 6-well culture dish. The medium is continually recycled over the surface of the cells and back into the medium container where it can be gassed. Medium will be gassed with preparations containing between 4% and 20% oxygen, 5% $CO_2$ and the remainder nitrogen. In this way, the cells can be maintained in the appropriate atmosphere such that the effect of the gas mixture can be determined. Growth rate may be determined by monitoring total cell protein per well.

ATP, ADP and AMP will be measured as described by Lundin et al., *Meth. Enzymol.* 133:27-41 (1986), using firefly luciferase. The ratio of NAD/NADH can be calculated from the ratio of lactate to pyruvate across tactic dehydrogenase and from the ratio of malate to oxaloacetate across malate dehydrogenase. The concentrations of these metabolites can be determined as taught by the methods set forth in *Methods of Enzymatic Analysis*, H. U. Bergmyer, ed., 3rd ed., Verlag Chemie, Weinheim, Vol. VI, pp. 570-588. The ratio of NADP/NADPH may be calculated from the ratio of isocitrate to alpha-ketoglutarate across isocitrate dehydrogenase and from the ratio of malate to pyruvate across malic enzyme. The determination of these metabolites is also set forth in *Methods of Enzymatic Analysis*. Energy change may be calculated from the equation. $(ATP+0.5\ ADP)/(ATP+ADP+AMP)$.

Besides looking at the oxygen dependence of the liver assist device, the devices will also be characterized with respect to their ability to simulate an isolated, perfused human liver. This includes testing the device for glucose and urea synthesis, bilirubin uptake and conjugation, and clotting factor biosynthesis as described above. Urea may be quantitated using a coupled glutamate dehydrogenase/urease assay. Glucose may be determined using a dye-coupled glucose oxidase assay. The assays for urea and glucose determination are found in *Methods of Enzymatic Analysis*.

As discussed earlier, the various vitamin K dependent clotting factors, prothrombin, factors VII, IX and X, as well as antithrombin III, can be determined using a solid phase radioimmunoassay as described by Kelly et al., *In Vitro Cell Dev. Biol.* 25:217-222 (1987). Antibodies for the immunoassay may be obtained from DAKO, Inc.

In a preferred LAD embodiment, the cell line HepG2/C3A is provided in a hollow fiber cartridge for use as a liver assist device. The device comprises hollow fiber capillaries contained within an extracapillary space. Media are circulated through the capillary space and cells are grown in the extracapillary space.

For the growth of cells, cells are seeded into the extracapillary space and supplied a constant inflow of fresh medium. 1400 cm$^2$ cartridges are inoculated with an effective number of cells, usually about $1 \times 10^9$ cells, and grown to confluence, usually about 14 days to about 21 days.

The medium supplied is generally a complex medium, usually a 3/1 mixture of Eagle's MEM and Earle's salts containing 10% defined/supplemented calf serum. This provides nutrients for cell growth. Thus, the cells grow on the outer surface of the capillaries. The hollow fiber cartridge containing the confluent cells is capable of functioning as a liver assist device for supporting a subject suffering from hepatic failure or insufficiency.

The cell lines may also find use as bioartificial livers or liver supports. In this manner, the cells are encapsulated or grown in hollow fiber capillary membranes for use as a bioartificial organ. The cells are encapsulated in biomaterials such as alginate-polylysine membranes, as taught by Cai et al., *Artifical Organs* 12:388-393; Sun et al., *Trans. Am. Soc. Artif. Intern. Organs Vol. XXXII*:3-9-41 (1986); O'Shea et al., *Biochimica Biophysica Acta* 804:133-136 (1984); Sun et al., *J. Controlled Release* 2:137-141 (1985); and U.S. Pat. No. 4,391,909. The encapsulated cells and vehicle capsules are then injected intraperitoneally into a subject.

The novel cell lines are useful for studies of human liver metabolism as well as the study of liver specific gene regulation. The cell line is originally derived from a human hepatoblastoma, not from a human hepatoma as is the usual case with human liver cell lines. Therefore, they are useful for studying all liver functions, including metabolic functions and liver specific gene expression. They also provide an useful in vitro liver model.

The cells and cell lines may also be used for studying the metabolism and/or toxicology of drugs or other pharmaceutical compositions. The cells, grown on a membrane or liver assist device, serve as a prototype artificial liver. Thus, the clinical indications of various drugs or compounds can be assessed in an in vitro model.

The cells grown in liver assist devices are also useful for the production of serum proteins. As indicated the cells exhibit liver specific biological activity and synthesize serum proteins, isoenzymes, clotting factors and the like. Accordingly the cells can be utilized as an in vitro factory for these proteins. In this manner the supernatant fluid is recovered from the cell culture and the plasma proteins isolated and purified. For convenience, the cells may be grown on a semipermeable membrane which allows for diffusion of serum proteins across the membrane where they are isolated and purified for further use.

As the cells are capable of functioning as a liver model they are also useful for studying viral hepatitis. This is particularly true as the cell lines are not transformed by hepatitis B virus and do not carry any HBV sequences.

The liver cells disclosed in the present invention have advantages over other systems known in the art, such as the isolated perfused rat liver (IPRL). The cultures are permanent. That is they have an indefinite life-span thereby allowing the effects of long-term exposure to be studied in an experimentally rigorous situation. Monolayer cultures of the permanent cell lines are typically maintained for several months and a liver assist device prepared according to the methods of the invention functions normally over at least an indefinite period, generally eight weeks, as determined by albumin production and glucose utilization. Use of the culture methods of the invention reduces the need for the regular sacrifice of animals required for liver perfusion, which comports with current U.S. government goals (NIH Guide for Grants and Contracts, supra). Finally, the cartridges containing cultured cells of the invention reflect human metabolism more closely than the isolated perfused livers from other species.

The methods of the invention, particularly the use of a hollow fiber based system, offers several advantages as liver assist devices. Cartridges support the growth of very high density cultures. Based on the extracapillary volume, 15 to 20 g of cells can be grown in a 1400 $cm^2$ unit and 100 g of cells can be grown in a 7000 $cm^2$ unit. This is in part based on the amount of albumin produced per day in the 1400 $cm^2$ unit (see Example II, below). The unit is capable of achieving sufficient cell mass to provide liver support to a subject suffering from liver failure.

Cartridge-grown cells are polarized and their growth approximates normal liver structure. The cells receive nutrients from the capillary space and secrete waste products into the extracapillary space (ECS). The ECS can be perfused to prevent the accumulation of toxic products.

The continual flow of media and the in-line oxygenator provide a more constant supply of oxygen and energy. The critical role of oxygen in liver metabolism is well documented in the IPRL literature, defined on previous pages, but has been largely ignored in the cell culture literature. For example, conventional cultures of HepG2/C3 or HepG2/C3A are oxygen (and therefore energy) limited. The constant circulation of oxygenated media fulfills the metabolic needs of the cells (Wöfle, D. et al. *Eur. J. Biochem.* 151:299-303 (1985)). If additional oxygen carrying capacity is required, the use of red blood cells or dissolved hemoglobin is provided, as described for perfused organs (Gores, G. J. et al *Hepatology* 6:511-517 (1986)).

Having now generally described the invention, the same will be more readily understood through reference to the following example which is provided by way of illustration, and is not intended to be limiting of the present invention, unless specified.

EXPERIMENTAL

EXAMPLE 1

Selection Scheme for HepG2/C3A

HepG2 cells were plated at a density of 0.5 cells/$cm^2$ in five 150 mm tissue culture dishes. One hundred individual colonies were removed from these plates with cloning rings. Colonies were initially chosen for a wide range of morphologies, ranging from flatteried, epithelial like cells to rounded, loosely connected cells. These were grown to confluence in 24 well dishes and the supernatants tested for albumin production using a solid phase radioimmunoassay. A very wide range of production levels were found, ranging from 100 ng/mg total cell protein/24 hr to 25 µg/mg/24 hr. Ten is clones (C through L) were chosen with albumin production above 1 µg/mg/24 hr and subjected again to limiting dilution cloning to insure clonality. These ten clones were then analysed for albumin production, albumin-/AFP ratio at confluence and contact inhibition. The values for these parameters are shown in Table 1. Clone C3 was chosen for further analysis. G2/C3 cells were plated in medium that contained pyruvate and amino acid, but no glucose, as sources of energy. The complete formula for this medium is shown below. Serum was dialyzed to remove glucose and no other complex carbohydrate was added. Since cells require glucose for production of new nucleotides; etc., only cells which could synthesize glucose from pyruvate and amino acids would be expected to proliferate in this medium. From an initial plating of $30 \times 10^6$ cells, two colonies 13A and 3B, were isolated after six weeks in this medium. These cells are flattened and epithelial with small nuclei and prominent nucleoli. Approximately 10% of the cells are binucleated.

| Formula for Glucose free Medium | |
|---|---|
| | Per Liter |
| Calcium chloride | 0.12 g |

-continued

Formula for Glucose free Medium

| | Per Liter |
|---|---|
| Cobalt chloride | 2 μg |
| Copper sulfate | 0.6 mg |
| Ferrous nitrate | 0.5 mg |
| Potassium chloride | 0.25 g |
| Magnesium sulfate | 0.35 g |
| Sodium chloride | 6.8 g |
| Sodium bicarbonate | 2.2 g |
| Sodium phosphate, dibasic | 0.3 g |
| Zinc sulfate | 1 mg |
| Molybdic acid | 15 μg |
| Manganese chloride | 15 μg |
| Arginine | 126 mg |
| Cystine | 24 mg |
| Glutamine | 292 mg |
| Histidine | 42 mg |
| Isoleucine | 52.5 mg |
| Leucine | 52.4 mg |
| Lysine | 72.5 mg |
| Methionine | 15.1 mg |
| Phenylalanine | 33 mg |
| Threonine | 10.2 mg |
| Tryptophan | 10.2 mg |
| Tyrosine | 36 mg |
| Valine | 46.8 mg |
| Alanine | 8.9 mg |
| Asparagine | 15 mg |
| Aspartate | 13.3 mg |
| Glutamate | 14.7 mg |
| Glycine | 7.5 mg |
| Proline | 11.5 mg |
| Serine | 10.5 mg |
| All amino acids are the L enantiomer | |
| Biotin | 1 mg |
| D-Ca pantothenate | 1 mg |
| Choline chloride | 1 mg |
| Folic acid | 1 mg |
| Inositol | 2 mg |
| Nicotinamide | 1 mg |
| Pyridoxal HCl | 1 mg |
| Riboflavin | 0.1 mg |
| Thiamine HCl | 1 mg |
| Ascorbic acid | 125 μg |
| Ergocalciferol | 10 μg |
| Menadione | 100 ng |
| Tocopherol | 20 μl |
| Retinoic acid | 10 μg |
| Glutathione | 50 μg |
| Hypoxanthine | 200 μg |
| Linoleic acid | 5 μg |
| Lipoic acid | 10 μg |
| Thymidine | 25 μg |
| Sodium pyruvate | 1.1 g |

TABLE 1
Characteristics of the Various Clones of HepG2

| Clone | Final Density | Albumin | AFP | Ratio |
|---|---|---|---|---|
| C3 | 0.30 | 29.5 | 1.1 | 25.7 |
| D5 | 0.62 | 20.5 | 3.9 | 5.3 |
| E2 | 0.81 | 3.1 | 4.1 | 0.8 |
| F1 | 0.44 | 9.3 | 6.5 | 1.4 |
| G6 | 0.78 | 3.5 | 4.6 | 0.8 |
| H1 | 0.47 | 9.7 | 5.7 | 1.7 |
| I1 | 0.38 | 22.5 | 6.1 | 3.7 |
| J5 | 0.35 | 32.7 | 3.1 | 10.5 |
| K1 | 0.31 | 23.7 | 0.8 | 29.6 |
| L3 | 0.34 | 12.8 | 0.9 | 14.2 |

Density is reported as mg total cell protein/square centimeter. Albumin and AFP are reported as μg produced/mg total cell protein/24 hr.

TABLE 2
Comparison of HepG2 and G2/C3 and G2/C3A

| | HepG2 | G2/C3 | G2/C3A |
|---|---|---|---|
| Final Density | 0.7 | 0.3 | 0.3 |
| Albumin | 16.8 | 29.5 | 41.2 |
| AFP | 3.0 | 1.1 | 0.8 |
| Albumin/AFP | 5.6 | 25.7 | 51.5 |
| Fetal aldolase (ald C) | Yes | No | No |
| Growth in glucose free medium | No | No | Yes |

Therefore as indicated, the clonally derived cell lines, particularly HepG2/C3A, demonstrate high albumin production and a high albumin to alphafetoprotein ratio at confluence. The cell lines display many additional features of normal liver cells. The near normal levels of human albumin and other serum protein produced by the cells emphasize their potential for mimicking liver functions. As further demonstrated the HepG2/C3A cells carry out normal levels of central metabolic processes, including gluconeogenesis and urea synthesis. For these reasons, the present cell lines, particularly HepG2/C3A, offer distinct advantages over other cell lines known in the art, including HepG2, for simulation of the human liver, for use in experimental hepatology, and as our extracorporeal liver assist device.

EXAMPLE II

HepG2C3 Provides an In Vitro Model for Modulation of the Liver Cell Phenotype

When cultures of HepG2/C3 are plated at low density, they enter a period of rapid division characterized by a doubling time of 24 hr and by expression of several markers of the fetal hepatocyte including alphafetoprotein, aldolases A and C and pyruvate kinase K. As the culture becomes confluent, growth slows and a new steady state is established with a doubling time of over 200 hr. At the same time, a coordinated switch in gene regulation occurs resulting in a precipitous decline in the fetal proteins and an increase in their adult counterparts. As an example, the increase in albumin synthesis as the culture matures is shown in FIG. 1.

EXAMPLE III

HepG2/C3 Cells Maintain Liver-Specific Structure and Transport Processes in Culture In an effort to examine the potential of HepG2/C3 cells for use in a liver assist device, the activity of these cells as models of normal human hepatocytes in culture was investigated, with particular attention to several liver specific structural and transport phenomena.

A. Materials and Methods

Figure 2:
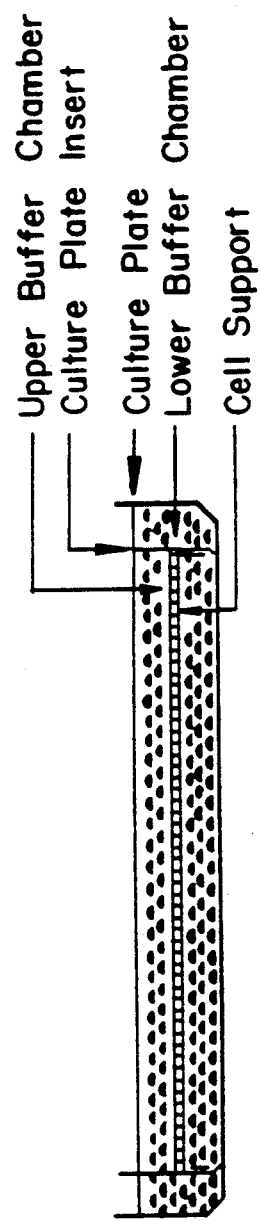
FIG. 2. Cross section of a culture well containing a Millicell TM insert. The cells were grown in the upper chamber, on the supporting membrane of the culture plate insert.

Millicell-CM ™ and Millicell-HA ™ culture plate inserts (12 mm diameter) were obtained from Millipore Corp., Bedford, Mass. The -CM inserts contain a nylon membrane which becomes clear when wet, but which must be coated with a biological material (e.g., collagen or extracellular matrix) before it will support cell attachment. The -HA membranes contain nitrocellulose which remains opaque but which supports cell attachment in the absence of coating (FIG. 2). The volume of culture medium in each chamber was 0.5 ml.

Tran$^{35}$S-label ™ (containing >1,000 Ci/mmol of methionine) was obtained from ICN (Irvine, Calif.). [2,4,$^3$H]-cholic acid (10–25 Ci/mmol) was obtained from New England Nuclear (Boston, Mass.). Tissue culture media were obtained from GIBCO (Grand Island., N.Y.) and supplements were obtained from Hyclone (Logan, Utah). Matrigel ™, an extract of extracellular matrix produced by the Engelbeth-Holm-Swarm (EHS) tumor, was obtained from Collaborative Research (Bedford, Mass.). Anti-human albumin antibody was obtained from Atlantic Antibodies (Scarborough, Me.). All other chemicals, unless otherwise specified, were obtained from Sigma Chemical Co. (St. Louis, Mo.).

1. Tissue Culture

The HepG2/C3 subclone was selected for the study because of its well-regulated expression of liver-specified genes. The cells were grown in 12 mm culture plate inserts in MEM/MAB supplemented with 10% supplemented calf serum (Hyclone). The —CM inserts were coated with Matrigel in order to allow cell attachment.

2. Criteria of Cell Polarity

The trans-cellular pH gradient was used as a measure of the cells' ability to maintain an ion gradient across the epithelial layer. Media from the top and bottom chambers were collected independently. Since the volume in each chamber was only 0.5 ml, samples from three wells were pooled for pH measurement. The pH gradient across membranes with sub-confluent monolayers or with no cells attached was measured as a control.

3. Albumin Secretion

Confluent cultures are characterized by a dramatic decline in the rate of cell division and alphafetoprotein (AFP) synthesis, and a sharp increase in albumin synthesis. Since circulating proteins are presumed to be secreted from the sinusoidal aspect of the cell, vectorial albumin secretion was used as a marker of basolateral function. The proteins were measured by a solid phase radioimmunoassay which does not cross-react with bovine serum albumin

4. Methionine Uptake

Methionine uptake was also used as an indicator of basolateral membrane activity (Balcarova-Stander, J., et al., *EMBO J.* 3:2687–2694 (1984)). The cells were incubated in methionine-free medium for 1 hour. At the end of this period, medium containing 100 $\mu$Ci/ml of Tran$^{35}$S-label ™ was added to one of the chambers and the cultures were incubated at 37° C. Inserts were removed at 3, 5 and 10 minutes, rinsed twice in cold PBS, placed in 10 ml of Universol ™ (Schwartz/Mann Biotech, Cleveland, Oh.) and counted.

5. Cholic Acid Uptake and Secretion

These measurements were performed as described for suspension cultures (Tarao, K., et al., *Am. J. Physiol.* 243:253–258 (1982)). Medium containing 2 $\mu$Ci/ml [2,4$^3$H]-cholic acid was added to either the top or the bottom chamber and incubated at 37° C. for 30 minutes. After this loading period the inserts were washed twice in ice cold saline and kept on ice until ready for assay. Secretion was measured by adding warm medium to both chambers, incubating at 37° C. for five minutes, and counting the media in each chamber. Pilot experiments showed that less than 5%. of the label remained associated with the cells at the end of five minutes.

6. Electron Microscopy

Electron microscopic examination was performed using a JEOL JEM 100CX. The entire insert was placed in 2% glutaraldehyde for 10 minutes to allow fixation. The membrane was then removed from the insert and embedded in Araldite. The plastic membrane of the -CM insert could not be sectioned satisfactorily, so cells grown on these membranes were peeled off with their underlying Matrigel layer prior to embedding. Cells grown in -HA inserts were embedded with their nitrocellulose membranes.

B. Results

1. Criteria of Confluence

Since the —CM membranes become clear when wet, the cells could be inspected under an inverted microscope. In all cases, confluence was accompanied by diminished alphafetoprotein (AFP) secretion and an increase in albumin secretion (Kelly, J. H. et al., 1989, supra) and by the generation of a PH gradient. Hence, these criteria were used to assess confluence of the cells grown on the —HA (nitrocellulose) membranes. Cells plated at a density of $10^5$/ml usually reached confluence within 3 days. The criteria of cell polarity were similar whether the cells were grown on Matrigel or nitrocellulose. Therefore, unless otherwise specified, data are pooled.

2. Trans-cellular DH Gradient

In order to obtain sufficient medium for pH measurements, groups of three inserts were pooled. No pH gradient developed in inserts without cells, or before the cells reached confluence. Once confluence was achieved, the pH in the top chamber was persistently higher. Table 3 shows the result of 9 observations (three wells pooled for each measurement). The top chamber was an average of 0.038 units lower, representing a hydrogen ion concentration about 17% higher than the bottom is chamber.

3. Albumin Secretion

Confluent cells secreted albumin into both the upper and lower chambers. However, the top chamber persistently contained about 30% more human albumin than the bottom chamber (Table 1).

4. Methionine Uptake

Figure 3:
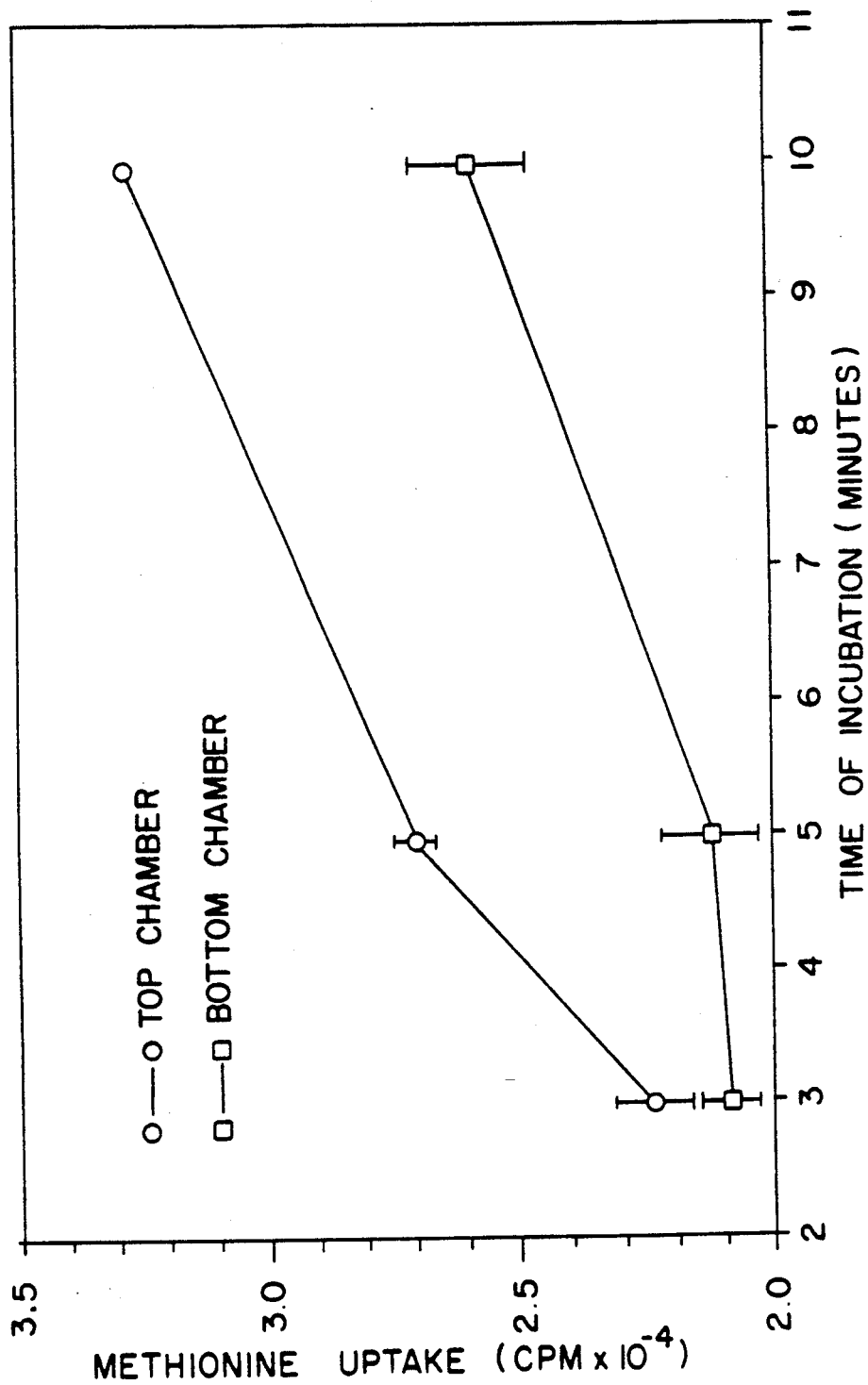
FIG. 3. Methionine uptake by HepG2/C3 cells from upper and lower chambers. After a 1 hour incubation in methionine-free medium, 100 $\mu$Ci/ml of Tran$^{35}$S-label TM were added to either the top or the bottom chamber, and the cells were incubated at 37° C. The inserts were removed at the indicated times, rinsed thoroughly in ice cold phosphate buffered saline and placed in counting solution. Each time point represents the mean ±SEM of 3 inserts.

Uptake of radiolabeled methionine, an indication of basolateral function, is shown in FIG. 3. Uptake from the top chamber was higher at all time points, 29% higher at 5 min and 26% higher at 10 min. No label was taken up by Matrigel or by the membranes alone.

5. Uptake and Secretion of Cholic Acid

After a 30 minute loading period, labeled cholic acid secretion was measured in the top and bottom chambers. Preliminary studies showed that over 95/10 of the label taken up during the labeling period was secreted within 5 min. The total counts taken up by the cells were therefore estimated by the sum of counts in the top and bottom chambers (Table 4). The highest uptake of cholic acid was from the bottom chamber (approx. 7200 cpm,vs 3200 cpm). However, 88% of the label was secreted back into bottom chamber, suggesting that minimal transepithelial transport was taking place. This is in sharp contrast to the top-loaded cells where 62% of the label was transported across the cell layer and secreted into the bottom chamber. Cholic acid was not taken up by Matrigel or the nitrocellulose membrane alone. The secreted label was unaltered cholic acid as assessed by thin layer chromatography.

TABLE 3 pH and Albumin Concentration in the Upper and Lower Chambers

| | Top Chamber | Bottom Chamber | n | p Value |
|---|---|---|---|---|
| pH | 7.650 ± 0.004 | 7.582 ± 0.007 | 9 | 0.006* |
| Albumin | 2.63 ± 0.05 | 2.00 ± 0.03 | 9 | 0.001* |

Numbers represent the mean ±SEM. p values were calculated using the paired Student's t-test. Cells were grown in 12 mm.Millicell inserts until confluence, and media was collected independently from the top and bottom chambers. pH measurements were performed on samples pooled from 3 wells, and albumin concentration was measured by solid phase RIA.

TABLE 4

Uptake and Secretion of $[2,4,^3H]$-Cholic Acid.

| | Total Uptake | Secreted Counts | | Transepithelial Transport | n |
|---|---|---|---|---|---|
| | | Top | Bottom | | |
| Top Loaded | 3,251 | 1236 ± 233 | 2015 ± 146 | 62% | 7 |
| Bottom Loaded | 7,247 | 866 ± 57 | 6381 ± 681 | 12% | 7 |

Medium containing 2 μCi/ml $(2,4,^3H)$-cholic acid was added to either the top or the bottom chamber and the cells were incubated at 37° C. for 30 min. After this loading period the inserts were washed twice in ice cold saline and kept on ice until ready for assay. Secretion was measured by adding warm medium to both chambers, incubating at 37° C. for 5 min, and assessing the radioactivity of the medium in each chamber. Less than 5% of the counts remained in the cells at the end of 5 min.

6. Ultrastructural Studies

Bile canaliculi surrounded by junctional complexes and showing normal microvilli were evident between cells. Incomplete canaliculi, characterized by a microvillous border, were also seen, and many of these appeared to open towards the lower chamber. The microvillous membrane was also the most active endocytotic membrane with numerous coated pits and vesicles. The development of bile ducts between cells was similar whether the cells were grown on Matrigel or nitrocellulose. However, the opening of incomplete bile canaliculi was not easily seen in cells grown on nitrocellulose because the cells tended to grow into the membrane.

DISCUSSION

The HepG2/C3 cell line has been examined a substitute for primary hepatocytes, as these cells demonstrate strong contact inhibition which is accompanied by a switch from the expression of fetal proteins to an adult phenotype. In addition, the cells express near-normal levels of liver proteins.

The non-specific markers of cell polarity included the pH difference between the top and bottom chambers, and the uptake of methionine. The H+ concentration in the bottom chamber was about 17% higher than that in the top chamber (Table 3).

Methionine uptake was 25-29% higher from the top chamber (FIG. 3), indicating that the basolateral membrane was oriented upwards (Balcarova-Stander, J., et al., *EMBO J.* 3:2687-2694 (1984)). The specific markers of liver polarity, albumin secretion and cholic acid transport, also indicated this orientation (albumin concentration was 30% higher in the upper chamber, and cholic acid transport was 5-fold higher in the top-to-bottom direction; see Tables 3 and 4).

Although most polarized cells grow with their basal membrane attached to the extracellular matrix (ECM), the tendency for HepG2/C3 cells to grow in the opposite orientation. is not altogether surprising. Hepatocytes do not normally rest on a dense basement membrane like that found in tubular organs, and their basal aspects are not characterized by the presence of hemidesmosomes. It has been thought for some time liver ECM differed qualitatively from other matrices (Roikind, M., et al., *J. Cell. Biol.* 87: 255-263 (1980)). However, recent reports suggest that the differences are quantitative and that liver ECM is a loose arrangement of the same constituents found in other tissues (Maher, J. J., et al., *Gastroenterology* 94:1053-1062 (1988); Bissell, D. M., et al., *Scand. J. Gastroenterol.* 23 (Suop. 151):1-7 (1988)).

The maintenance of the liver phenotype requires more than just a matrix interaction; cell-cell contact plays a major role. The HepG2/C3 cells are interesting in this regard. Although they are not dependent on liver ECM for growth or function, they are highly dependent on cell-cell contact. Cells seeded at low density form small colonies which do not spread over the plate. Furthermore, when the cells were grown on concentrated Matrigel, cord formation was observed. Thus, a single layer of ECM is insufficient to alter the intrinsic polarity of these cells, and the basolateral aspect formed preferentially in the unsupported environment of the upper buffer chamber.

The high uptake of cholic acid from the lower chamber (across the apical membrane) was unexpected. Three possible explanations are: (a) liver cells may have the capacity to absorb bile acids from the bile canaliculus; (b) the apical membranes in these cultured cellsmight contain significant levels of basal membrane proteins (incomplete polarity); or (c) the microvilli of the lower membrane may have increased the surface area to a point that cholic acid transport was increased by passive diffusion alone.

In summary, many of the criteria of polarity which are routinely applied to polarized cells in culture appear to be equally applicable to HepG2/C3 cells.

EXAMPLE IV

Metabolism in Normal Cultures of HeOG2/C3A is Oxygen Limited

Figure 4:
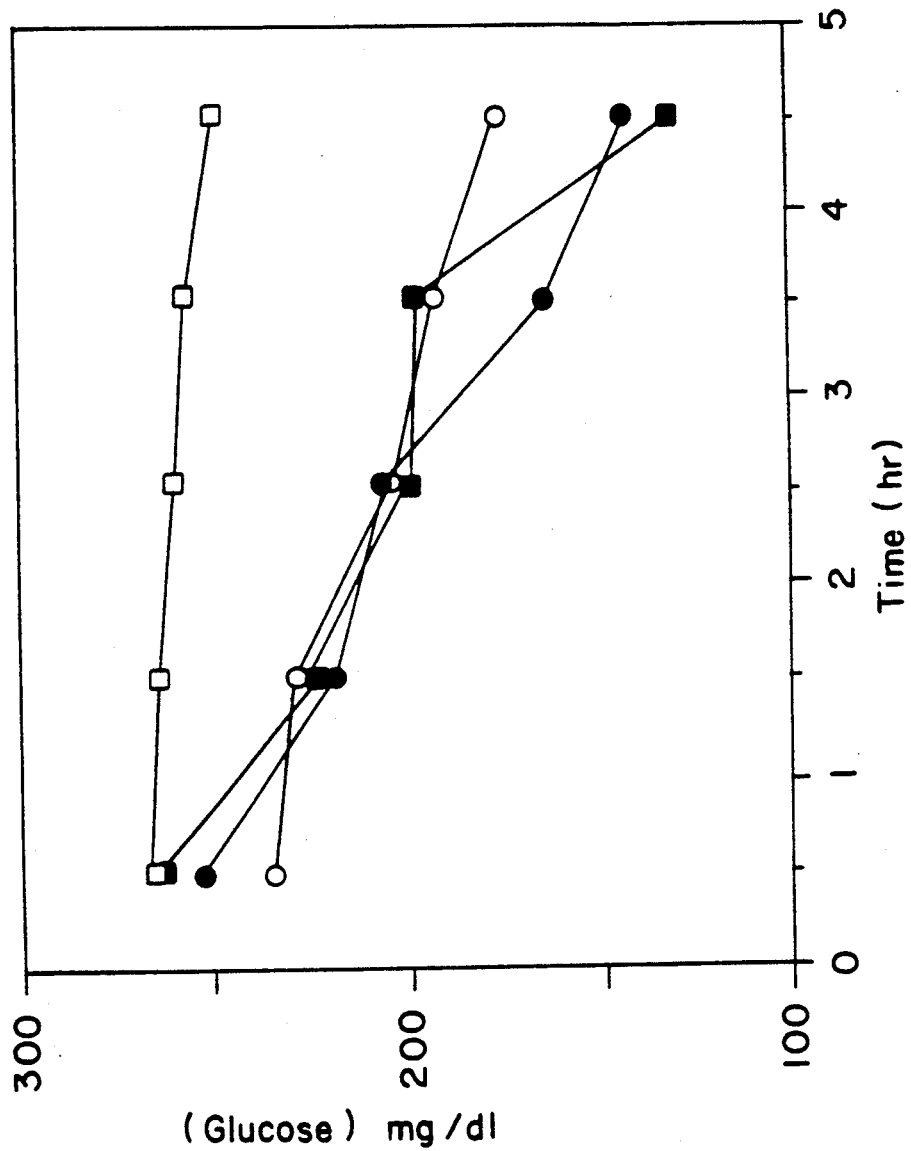
FIG. 4. Effect of nitropropionic acid on glucose utilization in HepG2/C3A cells. Confluent cell monolayers in 175 cm$^2$ flasks were incubated for 24 hr in the absence (squares) or presence (circles) of 1 mM nitropropionic acid (NOP). The medium was changed and incubation was continued in either regular medium (closed symbols) or in medium that had been gassed for 20 min before use of 95% oxygen, 5% carbon dioxide (open symbols).
■—Regular medium —oxygenated ● medium, —regular medium plus NOP, ○—oxygenated medium plus NOP.

In order to assess the feasibility of using HepG2/C3A as surrogate hepatocytes, several critical metabolic processes that any such cells would be required to perform were measured. FIG. 4 shows the result of a critical experiment demonstrating that, under standard cell culture conditions, the cells carry out primarily anaerobic metabolism. This surprising finding was first suggested by the initial measurements of glucose utilization in simple monolayers. Glucose concentration in the media fell to very low levels within 24 hr suggesting that glucose utilization was inefficient and that gluconeogenesis was not being performed. The logical explanation was that the cells were hypoxic and therefore unable to utilize the citric acid cycle. This hypothesis was tested in two ways:

First, glucose utilization was examined under both standard conditions and in media which had been oxygenated prior to incubation. As shown in FIG. 4, cells in the oxygenated medium used significantly less glucose.

In order to determine that the excess glucose utilization was due to failure of the cells to shunt pyruvate through the citric acid cycle, similar experiments were performed in the presence of nitropropionic acid (NOP). NOP is a transition state analog of succinate which irreversibly inactivates succinate dehydrogenase, preventing utilization of the citric acid cycle (Alston, T. A. et al. *Proc. Natl. Acad. Sci. U.S.A.* 74:3767-3771 (1977) Addition of this inhibitor would not have an effect under hypoxic conditions since the citric acid cycle would not be active. On the other hand, NOP should shift the glucose utilization curve in the oxygenated cultures so that it resembles the hypoxic curve. This curve is shown in FIG. 4.

A crucial variable in assessing metabolic activity in these cells is to ensure that the pathway is not oxygen (and therefore, energy) limited. The extent to which cells in culture may be oxygen limited is not widely appreciated. Glucose and urea synthesis from lactate were negligible in T-flasks in the absence of added oxygen. The remainder of the experiments presented below were performed in airtight vessels in a 95% $O_2$+5% $CO_2$ atmosphere using medium that had been gassed with the same mixture.

EXAMPLE V

HepG2/C3A Gluconeogenesis Activity

Figure 5:
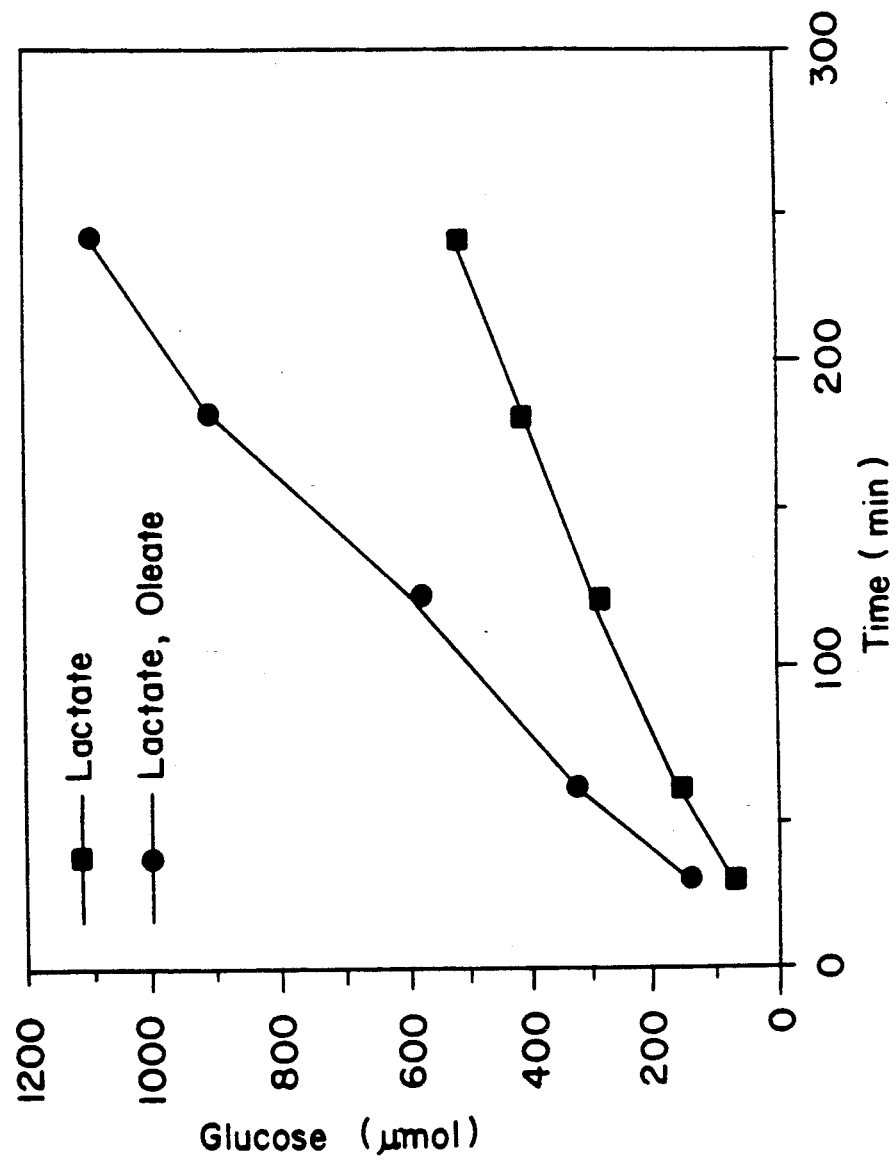
FIG. 5. Glucose synthesis by HepG2/C3A cells from lactate plus or minus oleic acid. Cells were incubated in Earle's balanced salt solution (EBSS) minus glucose in the presence of 5 mM tactic acid (squares) or 5 mM tactic acid, 1 Mm oleic acid (circles) in medium that had been gassed for 20 minutes before use with 95% oxygen, 5% carbon dioxide.

Glucose synthesis from lactate or amino acids is a major liver-specific metabolic function. FIG. 5 shows the rate of glucose synthesis from lactate in the presence or absence of oleic acid as an auxiliary energy source. As expected, oleic acid stimulates glucose production since the fatty acid can be used to supply energy for the process while lactate supplies the carbon. The rate of glucose synthesis measured in these experiments (1.13 mol/min/g from lactate, 2.44 mol/min/g from lactate plus oleate) is in good agreement with the rate found using either perfused rat liver or isolated rate hepatocytes (Krebs, H. A. et al. pp. 269-291 (1976)). It should be pointed out that this is a measurement of flux through an entire liver-specific pathway, not simply the level of a single enzyme. This indicates that the critical gluconeogenic enzymes, pyruvate carboxylase, phosphoenolpyruvate carboxy-kinase and fructose diphosphatase are all expressed and regulated appropriately in HepG2/C3/A cells.

EXAMPLE VI

Glycogen Synthesis in HeoG2/C3

It has been demonstrated (Newgard, C. B. et al. *Biol. Chem.* 258:8046-8052 (1983)) that, when glucose is administered to a starved rat, it is not resynthesized directly into glycogen as would be expected but is first degraded to pyruvate then resynthesized to glycogen. These experiments used a double labelling technique to quantitate the percentage of the administered glucose that first passed through the glycolytic pathway before being deposited as glycogen. Since these experiments were carried out in whole rats, a continuing question has remained as to the initial site of glucose metabolism. Glucose may be utilized first by a peripheral tissue such as muscle then sent back to the liver as lactate to be synthesized into glucose-6-phosphate and glycogen or, alternatively, glucose might be differentially utilized by different metabolic zones within the liver.

Figure 6A:
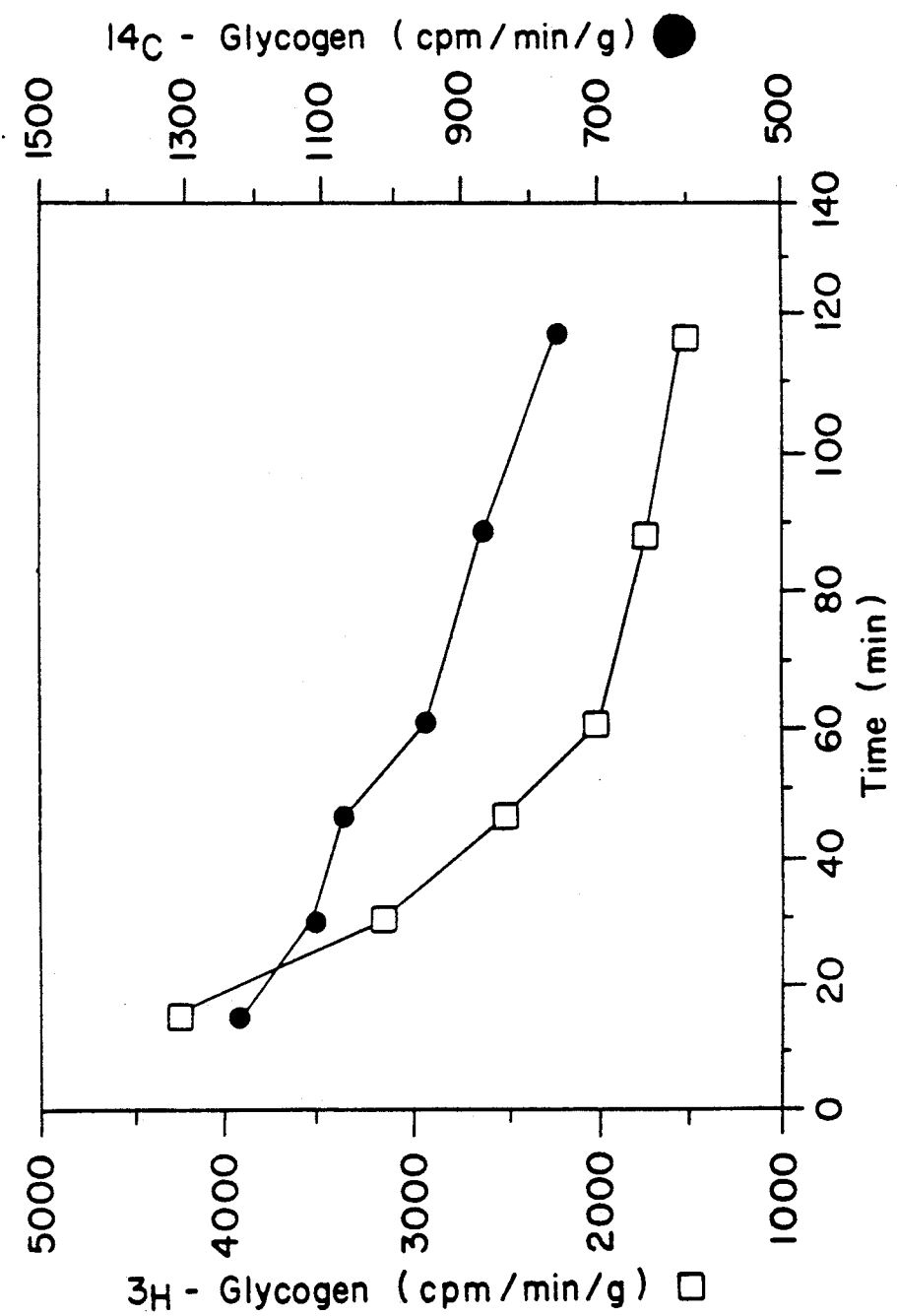
FIGS. 6A and 6B. Glycogen synthesis in HepG2/C3/cells. Confluent HepG2/C3A fells were incubated overnight in oxygenated EBSS minus glucose, containing 5 mM tactic acid and 1 mM oleic acid. At time zero, cells were fed with regular MEM/MAB medium, 10% serum which has a glucose concentration of 1.3 mM. At the indicated times after refeeding, 50 $\mu$Ci of $^3$H-water and 10 $\mu$Ci of 1-$^{14}$C-glucose were added. Cells were incubated for 15 min and glycogen was extracted by the method of Chan and Exton (See Example V, below). The $^3$H- or $^{14}$C-labelled glycogen was then counted in a liquid scintillation spectrometer.
Figure 6B:
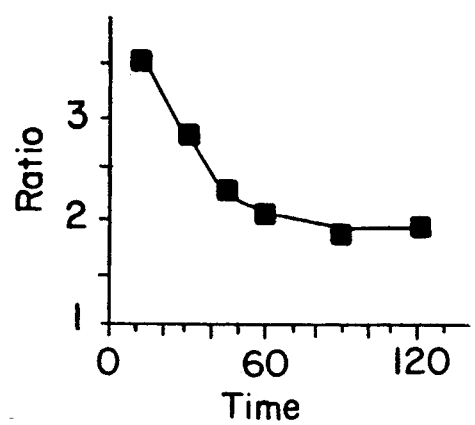

Using HepG2/C3A, similar double labelling studies have been performed (see FIG. 5B). These studies have demonstrated that the liver is capable of performing all of these metabolic interconversions. When $^{14}C$-glucose and $^{3}H$-water were administered simultaneously with a large amount of unlabelled sugar, the majority of the glucose was first degraded though glycolysis and then resynthesized to glycogen. This is indicated by the amount of 3H found in the glycogen. Glucose which is passed through glycolysis then resynthesized will have much more $^{3}H$ incorporated than will glucose which is used directly. When labelled glucose and $^{3}H$-water were administered varying lengths of time after the initial bolus of glucose, diminishing amounts of the carbohydrate were passed through glycolysis before deposition in glycogen, indicated by the declining amount of $^{3}H$ relative to $^{14}C$, shown in to FIG. 6B. These results indicate that glycolysis and gluconeogenesis can be active simultaneously but, with the addition of glucose, there is a gradual switch to direct glycogen synthesis.

EXAMPLE VII

Nitrogen Metabolism in HePG2/C3A

Figure 7:
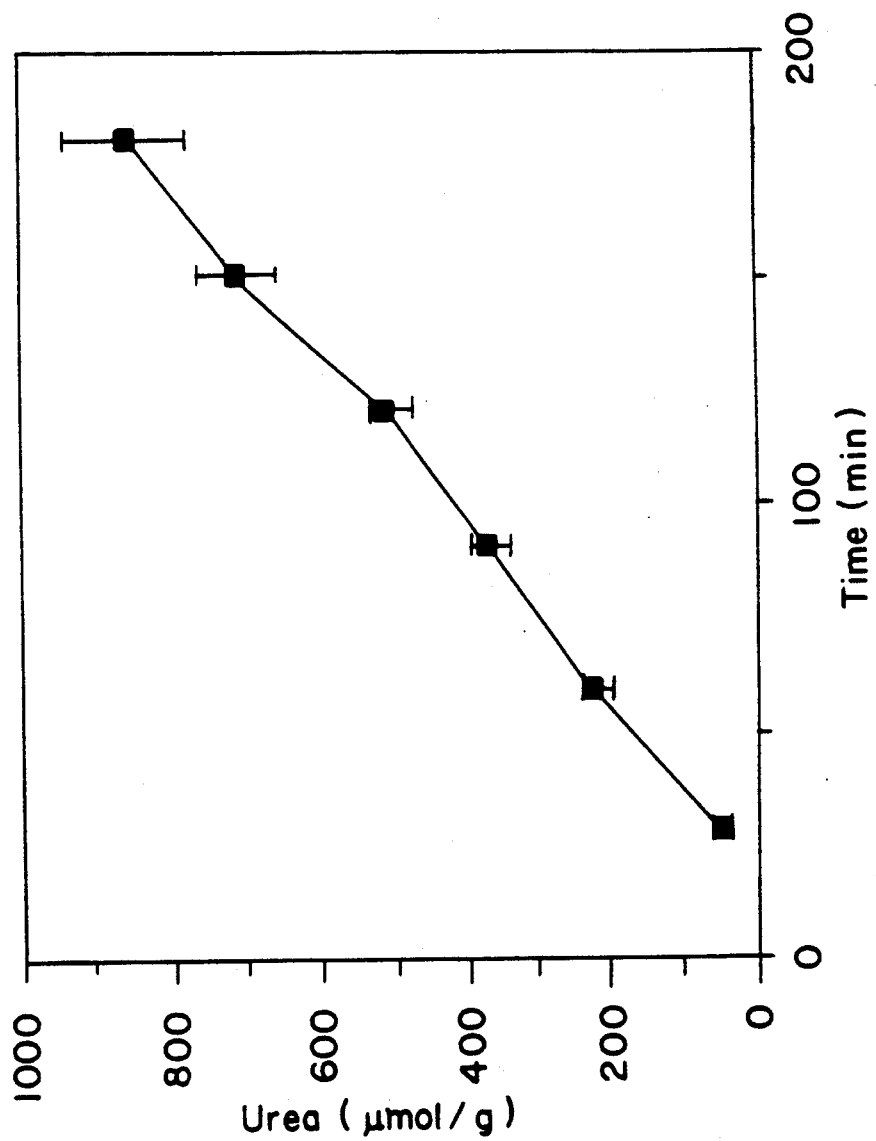
FIG. 7. Urea synthesis in HepG2/C3A cells. Cells were incubated overnight in EBSS minus glucose containing 5 mM lactate and 10 mM ammonium chloride which had been gassed with 95% oxygen, 5% CO$_2$ for 20 minutes before addition. At time zero, the cells were refed with the same medium. Aliquots were removed at the indicated times and assayed for urea production as described in Example VI, below. Each point is the average of triplicate determinations from two experiments. Each experiment is based on a single 850 cm$^2$ roller bottle containing approximately 2 g of cells.

The liver is the major organ for clearance of ammonia and other nitrogen containing compounds, and nitrogen imbalance is one of the more serious metabolic problems faced by the FHF patient. Therefore, the ability of HepG2/C3 to metabolize nitrogen in several forms was measured. FIG. 7 shows urea synthesis from lactate and ammonium chloride. The rate calculated from this experiment, 20 μmol/min/g cells, compares well with the rates measured in perfused rat livers and isolated hepatocytes (2 to 8 μmol/min/g liver (Krebs, H. A. et al. pp. 269-291 (1976))).

In another test of the ability of HepG2/C3A cells to metabolize nitrogen, the cells were incubated with a sample of serum from a patient in FHF. The pretreatment serum showed elevation of ammonia and several amino acids, notably phenylalanine and ornithine. After treatment of this serum with 0.5 g of HepG2/C3A cells for 3 hr, the ammonia was removed to below normal levels, urea was increased and the amino acids were reduced. It should be noted that phenylalanine, which has only one route of degradation through tyrosine under the action of phenylalanine hydroxylase, declined dramatically. Phenylalanine hydroxylase is dependent on tetrahydrobiopterin reductase to supply coenzyme for the reaction. Again, this is a measure of flux through a liver specific pathway and indicates that these cells achieve normal hepatocyte metabolism. Incubation of this FHF serum with the same mass of either HeLa cells or HepaSK cells (a liver endothelial cell line) showed no significant change in any of the measured parameters.

EXAMPLE VIII

HepG2/C3A Grown in Hollow Fiber Cartridges

Hollow fiber devices for cell culture have been used primarily for the growth of hybridomas in the production of monoclonal antibodies (Heifetz, A. H. et al. *Bio Techniques* 7:192-199 (1989)). Since these devices are equipped with an in-line oxygenation system, it was predicted that HepG2/C3 would perform better when grown in the hollow fiber device than in static culture. These devices also have the advantage of providing some of the three dimensional architecture of a normal liver. FIG. 8 shows the production rate of albumin by HepG2/C3A grown in an Amicon FloPath 1400 cartridge. The cartridge was inoculated with approximately $1 \times 10^9$ cells. Glucose utilization and albumin production were monitored daily thereafter. There is no way to accurately assess how many cells are resident in the cartridge when albumin production levels off after five weeks without destroying the culture. However, the extracapillary space were the cells grow is 20 ml in this device. Assuming that this entire space is filled with cells, the maximum number is about $20 \times 10^9$ or 20g of cells. Under normal culture conditions in T-flasks or multiwell dishes (which may be oxygen limited as discussed above) HepG2/C3A produce about 6 µg of albumin/mg wet weight of cells/24 hr in a confluent culture. HepG2/C3A cells grown in the hollow fiber cartridge, exceed this amount by a factor of two. This increase in yield of albumin/cell is probably due to the more physiologic culture conditions afforded by the hollow fiber device.

EXAMPLE IX

Treatment of Animals with Liver Dysfunction Using HeDG2/C3A Cells in a LAD

HepG2/C3A cells were grown to high densities in hollow fiber cartridges, as described in Example VII. This configuration allows the cells to function similarly to a perfused human liver, as an extracorporeal liver assist device (ELAD).

An ELAD prepared in this way, using methods described above, rescues animals in liver failure. A model using dogs injected with a sub-lethal dose of acetaminophen is utilized as described below and parameters of liver necrosis and function are monitored throughout the treatment.

A. Surgical Procedure

Under sterile conditions and general anesthesia, a shunt is created between the carotid artery and the internal jugular vein in a dog. An incision is made along the anterior border of the sternocleidomastoid and the carotid artery and internal jugular vein are exposed. Both vessels are ligated at the level of mandibular angle, and a shunt is fashioned between the two vessels. Silastic dialysis catheters are sutured in place, brought out through the incision and the wound is closed with 4/0 silk. The animals are observed until they recover from anesthesia and are examined again at six hours. Distress is monitored and acetaminophen (100 mg/kg) is administered q 6 hrs prn. The sutures are removed at one week and dialysis is not started until the shunt has matured. Attachment of the ELAD is performed by attaching the cartridge to the afferent and efferent limbs of the shunt via the dialysis catheters. The wound remains covered by surgical tape at all times to avoid injury to the shunt site.

B. Acetaminophen Poisoning

The injections of acetaminophen (750 mg/k for the first dose, 200 mg/k for the second two) are accompanied by a subcutaneous injection of 1% xylocaine to avoid a painful local reaction. The liver impairment in the group which receives the sub-lethal dose does not cause serious symptoms. The group which receives the lethal dose experiences anorexia, vomiting and diarrhea in the precomatose state. Additional drugs are not administered to the animals according to the model of Francavilla, A. et al. (*Gastroenterology* 96:470-478 (1989)). This is important only in the control animals; the animals who receive the liver dialysis are asymptomatic.

The ELAD is then used to remove toxins, conjugate bilirubin, restore a normal amino acid profile and replace serum proteins and clotting factors.

The ELAD is also used to support liver functions in anhepatic dogs given a lethal dose of acetaminophen. The dogs are kept alive by intermittent extracorporeal liver dialysis.

The Cell lines of the present invention overcome the problems of other cells used in liver assist devices. The present cells are permanent, they are able to duplicate vital biological functions of the liver, and are extremely well differentiated. When used in a liver assist device, the cells are capable of expressing liver-specific biological activities at a level effective to support a subject in hepatic failure or insufficiency for long periods. Thus, the present invention provides a method for supporting liver function. This provides sufficient time for liver regeneration to occur, as well as provides a better environment for liver regeneration by removing circulating toxins. Further, in those patients whose livers fail to regenerate, the patient can be kept alive while awaiting transplantation.

The method also provides a means of allowing patients to recover after liver failure before transplantation of a first liver. Also, in those patients who require emergency second transplants, the availability of a liver assist device would allow them to recover before undergoing a second round of major surgery.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A permanent human hepatocyte cell line constitutively having liver-specific biological activity at a level effective to support a subject suffering from hepatic failure or insufficiency, wherein said cell line is capable of growing in glucose-free media, and wherein at confluence, said cell line exhibits a rate of expression of albumin of at least about 20 µg/ml total cell protein/24 hours, and wherein said cell line produces albumin and alphafetoprotein such that the albumin to alphafetoprotein ratio is at least about 15.

2. The cell line of claim 1, wherein said rate of expression of albumin is at least about 25 µg/mg total cell protein/24 hours and said albumin to alphafetoprotein ratio is at least about 25.

3. The cell line of claim 1, wherein said cell line is HepG2/C3A having the identifying characteristics of ATCC No. CRL-10741.

4. In a liver assist device containing cells for supporting a subject suffering from hepatic failure or insufficiency, the improvement comprising cells of a permanent human hepatocyte cell line constitutively having liver-specific biological activity at a level effective to support a subject suffering from hepatic failure or insufficiency, wherein said cell line is capable of growing in glucose-free media, and wherein at confluence, said cell line exhibits a rate of expression of albumin of at least about 20 µg/ml total cell protein/24 hours, and wherein said cell line produces albumin and alphafetoprotein such that the albumin to alphafetoprotein ratio is at least about 15.

5. The liver assist device of claim 4, wherein said rate of expression of albumin is at least about 25 µg/ml total cell protein/24 hours and said albumin to alphafetoprotein ratio is at least about 25.

6. The liver assist device of claim 4, wherein said cell line is HepG2/C3A having the identifying characteristics of ATCC No. CRL-10741.

7. The liver assist device of claim 4, further comprising a semipermeable membrane having opposed first and second surfaces, wherein said cells are in contact with said first surface.

8. The liver assist device of claim 7, wherein said membrane comprises a tube and said first surface is the exterior surface of said tube.

9. The liver assist device of claim 8, wherein said liver assist device comprises a plurality of said tubes.

10. The liver assist device of claim 4, wherein said subject is a human.

11. A method for preparing a liver assist device having a membrane for supporting a cell line for supporting a subject suffering from hepatic failure or insufficiency comprising the steps of:
   (a) providing cells of a permanent human hepatocyte cell line constitutively having liver-specific biological activity at a level effective to support a subject suffering from hepatic failure or insufficiency, wherein said cell line is capable of growing in glucose-free media, and wherein at confluence, said cell line exhibits a rate of expression of albumin of at least about 20 µg/mg total cell protein/24 hours, and wherein said cell line produces albumin and alphafetoprotein such that the albumin to alphafetoprotein ratio is at least about 15, on a semipermeable membrane having opposed first and second surfaces; and
   (b) culturing said cells on said first surface until the cells reach confluence, said culturing step comprising the steps of:
      (i) seeding said first surface with said cells; and
      (ii) continuously circulating culture medium which supports the growth of said cells until the cells reach confluence.

12. The method of claim 11, wherein said rate of expression of albumin is at least about 25 µg/mg total cell protein/24 hours and said albumin to alphafetoprotein ratio is at least about 25.

13. The method of claim 11, wherein said cell line is HepG2/C3A having the identfying characteristics of ATCC No. CRL-10741.

14. A method for supporting a subject suffering from hepatic failure or insufficiency comprising the steps of:
   (a) contacting the blood of said subject with the liver assist device of claim 4,
      wherein said contacting causes molecules in the blood to contact said cells so as to achieve uptake and metabolic processing of said molecules in the blood, and said contacting further causes proteins and lower molecular weight molecules produced in said cells to enter the blood; and
   (b) removing excreted metabolic wastes from said liver assist device.

15. The method of claim 14, wherein said rate of expression of albumin is at least about 25 µg/mg total cell protein/24 hours and said albumin to alphafetoprotein ratio is at least about 25.

16. The method of claim 14, wherein said liver assist device further comprises a semipermeable membrane having opposed first and second surfaces, wherein said cells are in contact with said first surface, and wherein in said step (a) the blood is contacted with said second surface.

17. The method of claim 14, wherein said step (b) is performed by contacting a bathing solution with said cells to thereby remove said excreted metabolic wastes.

18. The method of any claims 14, 15, 16 or 17, wherein said method is performed extracorporaeally.

19. The method if performed of any of claims 14, 15, 16 or 17, wherein said method intracorporeally.

20. The method of any claims 14, 15, 16 or 17, wherein said cell line is HepG2/C3A having the identifying characteristics of ATCC No. CRL-10741.

21. The method of claim 11, wherein said subject is a human.

22. A method for producing serum proteins comprising the steps of:
   (a) maintaining a permanent hepatocyte cell line constitutively having liver-specific biological activity, wherein said cell line is capable of growing in glucose-free media, and wherein at confluence, said cell line exhibits a rate of expression of albumin of at least about 20 µg/mg total cell protein/24 hours, and wherein said cell line produces albumin and alphafetoprotein such that the albumin to alphafetoprotein ratio is at least about 15, in a nutrient culture medium;
   (b) recovering supernatant fluid from said culture;
   (c) separating plasma proteins from said supernatant fluid; and
   (d) purifying said plasma proteins.

23. The method of claim 22, wherein said rate of expression of albumin is at least about 25 µg/mg total cell protein/24 hours and said albumin to alphafetoprotein ratio is at least about 25.

24. The method of claim 22, wherein said cell line is HepG2/C3A having the identifying characteristics of ATCC No. CRL-10741.

* * * * *